United States Patent
Joh

(10) Patent No.: US 9,737,433 B2
(45) Date of Patent: Aug. 22, 2017

(54) DISPOSABLE WEARABLE URINARY COLLECTION APPARATUS

(71) Applicant: William Kyungha Joh, West Bloomfield, MI (US)

(72) Inventor: William Kyungha Joh, West Bloomfield, MI (US)

(*) Notice: Subject to any disclaimer, the term of this patent is extended or adjusted under 35 U.S.C. 154(b) by 0 days.

(21) Appl. No.: 15/144,889

(22) Filed: May 3, 2016

(65) Prior Publication Data

US 2017/0100276 A1    Apr. 13, 2017

Related U.S. Application Data

(60) Provisional application No. 62/284,848, filed on Oct. 13, 2015.

(51) Int. Cl.
*A61M 5/32* (2006.01)
*A61F 5/451* (2006.01)
*A61F 5/453* (2006.01)
*A61F 5/455* (2006.01)
*A61M 27/00* (2006.01)
*A61F 5/44* (2006.01)
*B65D 83/10* (2006.01)
*B65D 81/02* (2006.01)

(52) U.S. Cl.
CPC .............. *A61F 5/451* (2013.01); *A61F 5/453* (2013.01); *A61F 5/455* (2013.01)

(58) Field of Classification Search
CPC ........... A61M 5/32; A61M 27/00; A61F 5/44; B65D 83/10; B65D 81/02
See application file for complete search history.

(56) References Cited

U.S. PATENT DOCUMENTS

| 2,944,551 | A | * | 7/1960 | Breer | ...................... | A61F 5/455 |
| | | | | | | 4/144.1 |
| 4,239,044 | A | | 12/1980 | Pavlinch | | |
| 4,769,020 | A | | 9/1988 | Eaton | | |
| 4,863,449 | A | * | 9/1989 | Therriault | ............... | A61F 5/453 |
| | | | | | | 128/844 |
| 6,296,627 | B1 | * | 10/2001 | Edwards | ................. | A61F 5/453 |
| | | | | | | 604/322 |

(Continued)

FOREIGN PATENT DOCUMENTS

WO        2006077351 A1    7/2006

*Primary Examiner* — Tatyana Zalukaeva
*Assistant Examiner* — Ilya Treyger
(74) *Attorney, Agent, or Firm* — Carrier Blackman & Associates, P.C.; Joseph P. Carrier; Jingli Wang

(57) ABSTRACT

A urinary receptacle includes an elongate, tubular main body having a closed upper end and an open lower end; a tubular port in fluid communication with the main body, the tubular port being configured to receive a user's penis therein in a fluid-tight manner; a urine collection receptacle connectable to the lower end of the main body which receives and stores the urine therein; and a fastener which secures at least one of the main body and the urine collection receptacle to the user or a garment worn by the user. The apparatus is simple to use, and is manually accessible for handling though modified side pockets of a pair of pants or other such conventional garment worn by the user. The main body, tubular port, and storage receptacle are formed of flexible, waterproof material and are configured to collapse flat against a user's body when not in use.

14 Claims, 4 Drawing Sheets

(56) References Cited

U.S. PATENT DOCUMENTS

| | | | |
|---|---|---|---|
| 7,077,833 B2 * | 7/2006 | Bonham | A61F 5/449 604/323 |
| 8,603,056 B1 * | 12/2013 | Fallis | A61F 5/455 604/318 |
| 2005/0101924 A1 | 5/2005 | Elson et al. | |
| 2008/0015528 A1 | 1/2008 | Chang | |
| 2008/0269548 A1 | 10/2008 | Vecchiotti et al. | |
| 2011/0152802 A1 | 6/2011 | DiCamillo et al. | |
| 2012/0029452 A1 | 2/2012 | Rodsten | |
| 2013/0237964 A1 | 9/2013 | Kicos | |
| 2013/0338617 A1 | 12/2013 | Newton, Jr. | |
| 2014/0163498 A1 | 6/2014 | Natusch | |

* cited by examiner

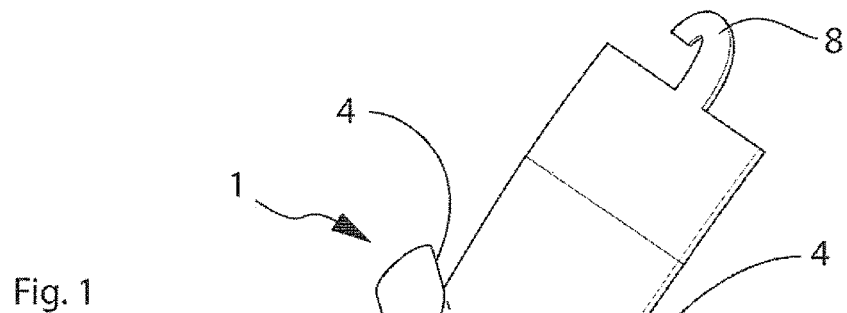
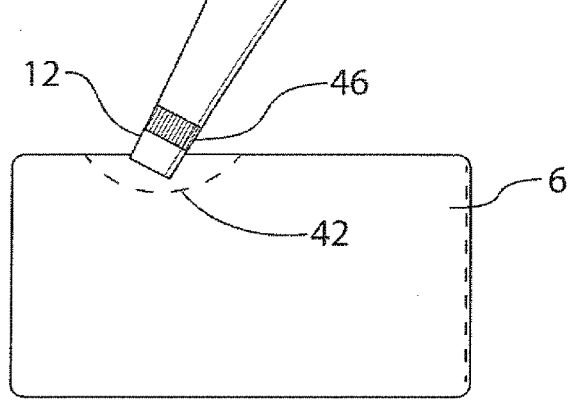
Fig. 1
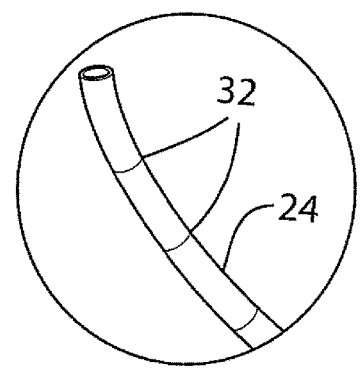
Fig. 1B
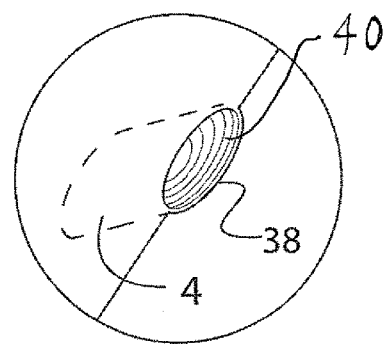
Fig. 1A

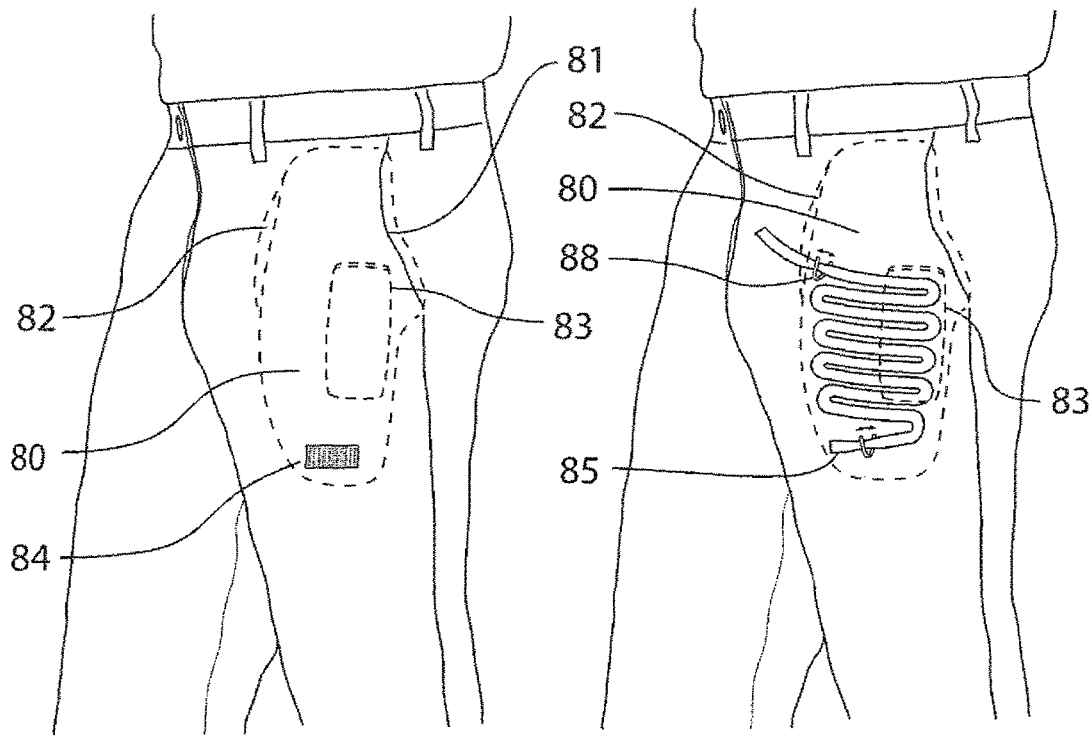
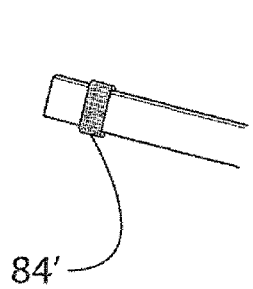
Fig. 7
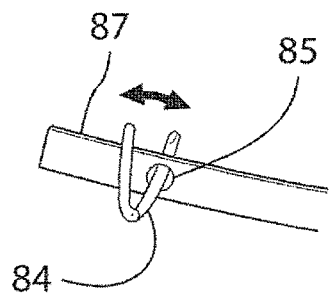
Fig. 6

DISPOSABLE WEARABLE URINARY COLLECTION APPARATUS

CROSS REFERENCE TO RELATED APPLICATIONS

This application claims priority under 35 USC §119(e) from U.S. Provisional Patent Application No. 62/284,848, filed 13 Oct. 2015, the entire disclosure of which is incorporated herein by reference.

BACKGROUND OF THE INVENTION

1. Field of the Invention

The present invention relates to an apparatus which may be inconspicuously and conveniently worn by a male or female person beneath regular clothing for receiving and storing urine discharged by the person. More particularly, the present invention relates to a disposable and wearable apparatus of the type described, which can be used by both male and female users who have urinary incontinence or urinary urgency while usual private access for voiding is not available, is simple to use, and is manually accessible for handling though modified side pockets of a pair of pants or other such conventional garment worn by the user.

2. Description of the Background Art

A great number of urinary receptacles for men and women suffering incontinence have been on the market for many years and a number of different approaches have been tested, including the basic diaper type products which include liquid-absorbing materials and are worn in contact with a person's genitals. There are various other known devices which are worn by a person beneath the normal clothing some of which include a liquid receptacle that collects urine discharged by the person and which may be subsequently disposed of or emptied for reuse, others of which may be extended over the male organ similar to a condom and which are elongate so that they can channel any discharged urine downwardly to an opening near the person's feet or to a receptacle secured to the person at a lower level, and some devices which may require the assistance of a medical professional such as a catheter. See, for example, the devices disclosed in U.S. Pat. No. 3,356,091, US Published Application Nos. 2008/0015528, 2011/0152802, 2012/0029452, 2013/0237964, 2013/0338617, 2014/0163498, and WO2006077351.

While each of these devices may serve the intended purposes, there are some drawbacks associated therewith. For example, most of the known devices are relatively bulky such that a user feels encumbered when wearing same and at least some part of the device projects away from the user's body, especially in the genital area, so that it becomes conspicuous to others that the person is wearing same, while the conventional apparatus tend to be inconvenient and conspicuous when accessing same for adjustment and the like. Also, some of these devices may remain attached to a person's urinary organ which may become uncomfortable and may lead to other problems such as urinary tract infections. With condom type urinary receptacles that are disposed over the male organ, there may be friction between the male organ and the condom including any adhesive associated therewith, such that inflammation and irritation of the male organ may occur. Further, it may become difficult to attach and detach the device to the male organ if it becomes necessary to use the device multiple times while it is being worn by the person for an extended period. Also, some traditional urinary receptacles such as catheters require the assistance of medical professionals, which makes use of same challenging.

Thus, a need still exists in the art for a wearable urinary receptacle, which may be inconspicuously and conveniently worn by a male or female person beneath regular clothing for receiving and storing urine discharged by the person, which may be used by essentially any person, which may be conveniently attached and detached to the person's urinary organ multiple times during an extended period of use, which is simple to use, and which may be conveniently and inconspicuously accessed for manipulation while being worn by a user.

SUMMARY OF THE INVENTION

The present invention has been developed in order to fulfill the discussed need.

An object of the present invention is to provide a collapsible, flexible urinary collection apparatus which may be inconspicuously and conveniently worn by a male or female person beneath regular clothing for receiving and temporarily storing urine discharged by the person, and which may be easily and inconspicuously manually manipulated by the person for being attached and detached from the person's urinary organ without the removal or partial removal of clothing, e.g., by hand(s) which are inserted into side pocket(s) of pants worn by the user and which have opening(s) to access the apparatus.

Another object of the invention to provide such an apparatus which is disposable and economical to produce.

According to a first aspect of the present invention, the urinary collection apparatus comprises an elongate, tubular main body having an upper portion with a closed upper end and a lower portion with an open lower end; a tubular port connected to the upper portion of the main body and configured to receive a user's penis therein in a fluid-tight manner such that urine discharged from a penis flows into the main body via the tubular port; a urine collection receptacle connectable to the lower portion of the main body, and which receives and stores urine which flows out of the open lower end of the lower portion; and fastening means for securing at least one of the main body and the urine collection receptacle to a user or a garment worn by the user,
wherein the main body, tubular port, and storage receptacle are formed of flexible, waterproof material and are configured to collapse flat against a user's body.

According to a second aspect of the invention, in addition to the first aspect, the tubular port is tapered along a length thereof with a largest diameter portion directly adjacent to the main body and a smallest diameter portion furthest away from the main body and having an end opening, whereby the user's penis can be snugly fitted into some portion of the tubular port.

According to a third aspect of the invention, in addition to the first aspect, a projecting end of the tubular port has an opening into which the user's penis may be inserted, and an elastic resilient material is provided around a circumference of the tubular port which urges the circumference radially inward.

According to a fourth aspect of the invention, in addition to the first aspect, a plurality of the tubular ports are provided in fluid communication with the main body and projecting away therefrom, the plurality of tubular ports having different size diameters.

According to a fifth aspect of the invention, in addition to the first aspect, the urinary collection apparatus further comprises a wrap that may be selectively secured around the user's penis and which sealingly contacts an inner surface of the tubular port when the user's penis is inserted in the tubular port.

According to a sixth aspect of the present invention, in addition to the first aspect, the storage receptacle may be selectively attached and detached from the main body.

According to a seventh aspect of the present invention, in addition to the first aspect, the urinary collection apparatus may further comprise an undergarment which may be worn by a male user and to which the main body, the tubular port, and the storage receptacle may be selectively attached and detached.

According to an eighth aspect of the present invention, in addition to the first aspect, the urinary collection apparatus may further comprise an undergarment which may be worn by a female user, including a main portion which is configured to extend over the female user's genital area, and a spout which is fluidly connectable to a central part of the main portion, projects away therefrom, and may be selectively inserted in the tubular port.

According to a ninth aspect of the present invention, in addition to the first aspect, the urinary collection apparatus may further comprise an outer garment which may be worn by the user about his/her lower body, wherein the outer garment has at least one side pocket having an outer opening through which the user may insert his or her hand, and an inner opening through which the user's hand may access the apparatus, and wherein the lower portion of the main body and the receptacle may be disposed in the side pocket during use of the apparatus. In a modification, the lower portion of the main body may have a closed end and the receptacle may be omitted, and in such case only the closed ended lower portion of the main body may be disposed in the side pocket during use of the apparatus.

Such urinary collection apparatus according to the first-ninth aspects of the present provides a number of advantages. For example, such collection apparatus may be conveniently, comfortably, and inconspicuously worn by essentially any male or female user who suffers from incontinence because it is formed of flexible, waterproof material and its parts are configured to collapse flat against a user's body when not in use, and the tubular port(s) thereof may be properly fitted to any size male or female genitals in a fluid-tight manner. As other examples, a user may conveniently manipulate the apparatus relative to the user's genitals while the apparatus is being worn by the user, e.g., via a pocket of pants being worn by the user, and the users may even choose to relieve themselves normally in a toilet while wearing the apparatus. Still further the collection receptacle may be conveniently removed for emptying or for being discarded and replaced, while the other components of the apparatus remain attached to a user. As another example, the apparatus may be constructed of inexpensive materials, such as plastic film materials, and disposed of after a single use.

The above advantage and other advantages and features of the present disclosure will be readily apparent from the following detailed description of the preferred embodiments.

Intent of Disclosure

Although the following disclosure offered for public dissemination is detailed to ensure adequacy and aid in understanding of the invention, this is not intended to prejudice that purpose of a patent which is to cover each new inventive concept therein no matter how it may later be disguised by variations in form or additions of further improvements. The claims at the end hereof are the chief aid toward this purpose, as it is these that meet the requirement of pointing out the improvements, combinations and methods in which the inventive concepts are found.

There have been chosen specific exemplary embodiments of a urinary collection apparatus according to the present invention and specific alternative structures and modifications thereto. The exemplary embodiments chosen for the purposes of illustration and description of the structure and method of the invention are shown in the accompanying drawings forming a part of the specification.

BRIEF DESCRIPTION OF THE DRAWINGS

FIG. 1 is an exploded side perspective view of a urinary receptacle apparatus in accordance with an exemplary embodiment of the present disclosure;

FIG. 1A is a perspective view of a modification to a tubular port of the exemplary embodiment of FIG. 1;

FIG. 1B is a perspective view of a modification to a lower portion of a main body of the exemplary embodiment of FIG. 1;

FIG. 4 is a front elevational view of an exemplary embodiment of a garment pocket which may be used as another component of a urinary receptacle apparatus according to the present invention.

FIG. 5 is a front elevational view of the garment pocket of FIG. 4 together with a modification of a portion of the urinary receptacle apparatus of FIG. 1.

FIG. 6 is an enlarged front elevational view showing how the components in the modified exemplary embodiment of FIG. 5 may be coupled together.

FIG. 7 is similar to FIG. 6 and shows a modification of the embodiment in FIG. 6.

DETAILED DESCRIPTION OF EXEMPLARY EMBODIMENTS

Figure 2A:
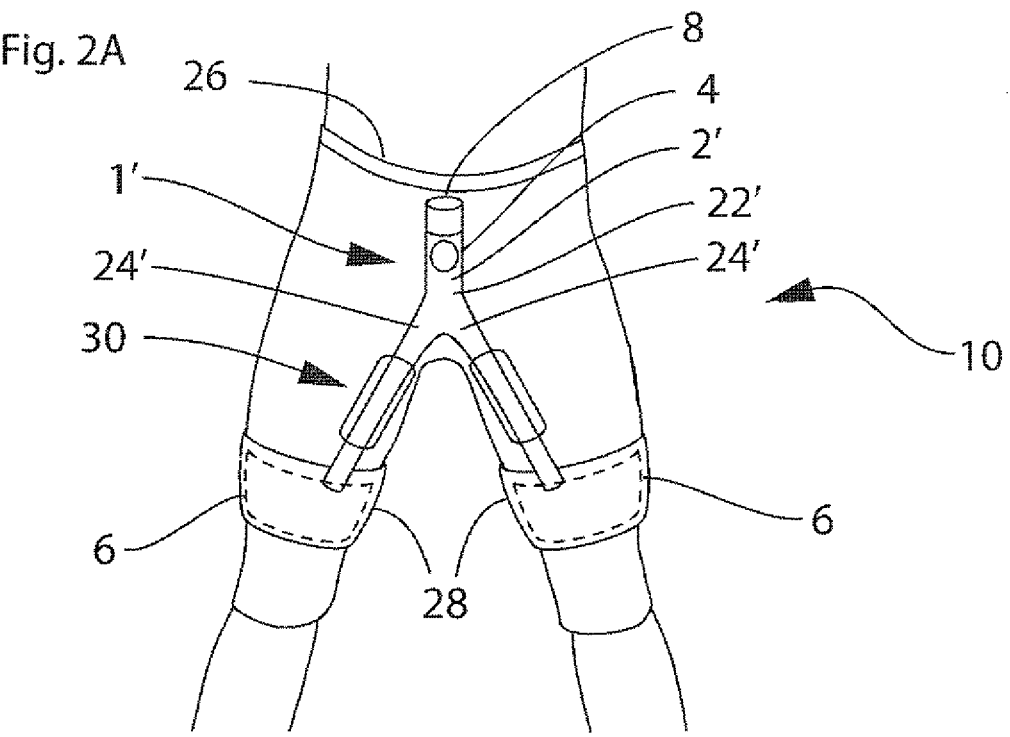
FIG. 2A is a front elevational view of a urinary receptacle apparatus for males according to another exemplary embodiment of urinary receptacle in accordance with the present invention.

As those of ordinary skill in the art will understand, the combinations of features illustrated provide representative embodiments for typical applications. However, various combinations and modifications of the features consistent with the teachings of the present disclosure may be desired for particular applications or implementations.

FIG. 1 is an exploded side perspective view of a urinary collection apparatus 1 which may be used by male or female persons in accordance with one exemplary embodiment of the present invention. The urinary collection apparatus 1 may generally include a main body 2, at least one tubular port 4 connected to the main body and projecting therefrom, a urine collection receptacle 6, and securing means for securing the apparatus to a person, such as a fastener 8 which my be used to connect an upper portion of the main body to a an under garment or other garment being worn by the person. The securing means may include other components, e.g., the modified embodiment shown in FIGS. 2A, 2B includes a special under garment 10 which the person would wear and to which the urinary collection apparatus 1 may be connected, as discussed further below.

The urinary collection apparatus 1 may preferably be constructed of flexible and collapsible material(s) which generally remain flat and inconspicuous when the apparatus is worn by a person. Such material(s) may be any suitable material(s), e.g., any suitable type of plastic, plastic-like, rubber, elastomeric, or polymeric material(s), which material(s) may possess or be treated to possess anti-bacterial properties. The apparatus 1 may be relatively inexpensive to construct from such material(s), so that it may be disposed of after a single use/wearing, but may be cleaned and reused if desired. Due to the low cost of the materials used to make the urinary collection apparatus 1 in this exemplary embodiment, a user may choose to dispose of the apparatus, or at least some portion(s) thereof such as the storage receptacle 6, after a single use. The urinary collection 1 apparatus may be transparent or any desired color.

The Main Body

The main body 2 may include a larger diameter upper portion 22 to which the tubular port(s) 4 are connected and a lower portion 24 which may taper downwardly to a smaller size and may terminate at a lower open end 12. The lower open end 12 may be in fluid communication with the storage receptacle 6. In terms of shape, the upper portion 22 may be substantially straight such that it may hang directly in front of a user's genitals, and the lower portion 24 may divert left or right toward either of the user's legs, to which the storage receptacle 6 may be secured in any appropriate manner. Such arrangement is generally shown in the modified embodiment of FIG. 2A, although in such modification the main body includes two lower portions 24 which extend toward the user's legs, respectively.

The main body 2 may be formed as a tubular sleeve of thin, flexible, waterproof material configured to collapse flat against a user's body when not in use. For example the main body may be formed of pliable sheet material(s), which may include a single layer or multiple layers laminated together, and which is leak-proof to urine and to other liquids. As another example, the main body 2 may be made from stretchable and resilient materials including but not limited to rubber, latex, and elastomeric materials so that it can expand as urine is flowed into it. The upper and/or lower portions of the main body 2 may be constructed from more than one material. Generally, the material(s) used for the main body should be flexible and sufficiently strong and/or stiff so that the main body will retain its shape during any normal physical activities that the user may engage in. Based on its smaller size, the lower portion 24 and especially the lower open end 12 thereof, may be constructed to be stronger and/or stiffer than the larger upper portion 22 to assure that urine may flow unobstructed therethrough, can be repeatedly attached and detached to the storage receptacle 6, and is more resistant to kinking or tangling in its use. While the main body 2 may be sufficiently thin, flexible, and collapsible so that it is unencumbering and inconspicuous in use, again, it should be sufficiently thick and strong that it is not susceptible to leakage and retains its shape under the forces typically encountered in use thereof.

A diameter of the main body 1 may vary. Generally, the upper portion 24 is sufficiently large so that the tubular port 4 which connects and extends into the upper portion 22 may accommodate a large male organ—penis, or at least a distal portion thereof. For example the upper portion may have a diameter of 8-12 cm and a length of 10-30 cm. The lower portion 24 may then taper to become progressively smaller. For example, the upper end of the lower porion 24 may have the same diameter of the upper portion, then taper downwardly through a length of 10 cm or more to a lowermost diameter of 1.0-2.0 cm at the lower open end 12. For an average sized user the lower portion 24 may extend to a mid-thigh, where it would extend into the storage receptacle 6, which receptacle may be secured to the user's thigh or under garment.

When not being used for receiving and channeling urine, the main body 2 collapses flat against the body or under garment of a person wearing the apparatus 1, such that it does not protrude and is inconspicuous. When the main body 2 is being used to collect and channel urine, it will expand slightly as the urine passes through it, but still does not protrude to any appreciable extent and remains inconspicuous.

The upper end of the main body 2 may be closed using any appropriate sealing means such as adhesive or heat to bond the walls of the pliable sheet material together, and a fastener 8 such as a hook, a hook-and-loop fastener, button, etc. may be connected to the upper end of the main body for securing same to a waistline of a garment or under garment worn by the person. With the closed upper end being spaced above the position of the tubular port as shown, any urine in the main body is prevented from leaking from the upper portion of the main body above the port 4. As reflected in FIG. 2A, when the main body 2 is so connected to the garment or under garment worn by the user at substantially a same level as a waistline 26 of the garment, through the fastening means 8 provided on the closed upper end of the main body, the port 4 is conveniently disposed at substantially a same level as the user's penis. The lower portion of the main body may taper downwardly to a smaller size and terminate at the lower open end 12 which is in fluid communication with the storage receptacle 6.

The lower portion 24, the lower open end 12, and/or the storage receptacle 6 may be provided with a check valve or one-way valve (not shown) to prevent urine from traveling upwardly therein.

Figure 2B:
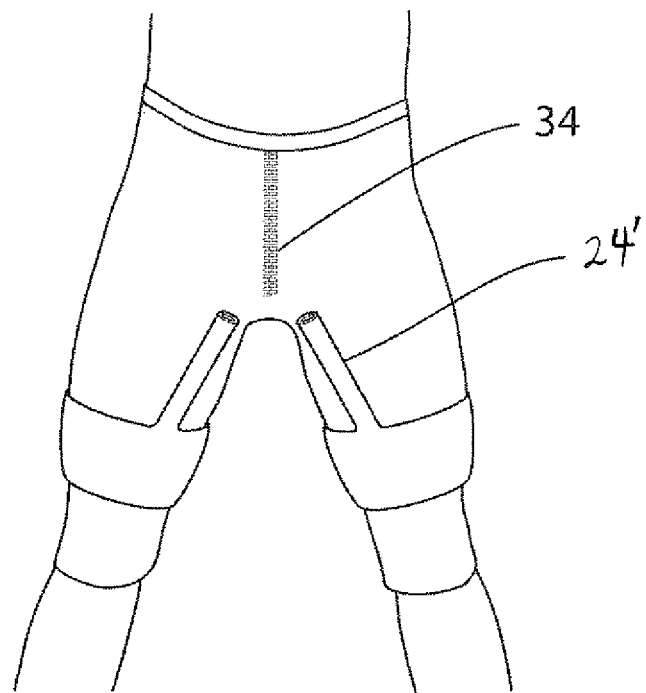
FIG. 2B is a front perspective view of the urinary receptacle apparatus according to the exemplary embodiment of FIG. 2A, but with some components removed for ease of understanding.

While the structure of the exemplary embodiment of the urinary collection apparatus 1 shown in FIG. 1 has been described, it will be apparent to persons of ordinary skill in the art that many modifications and variations may be made thereto with out departing from the intention and gist of the disclosed invention. For example, and with reference to FIGS. 2A, 2B, there is shown a special under garment 10 which the person would wear and to which the urinary collection apparatus 1 or a modified version 1' of the apparatus may be secured such that the tubular port 4 connected to the main body 2' is disposed directly in from of a fly opening 34 of the garment. In FIGS. 2A, 2B a modified version of the urinary collection apparatus is depicted in which the main body 2' includes two of the lower portions 24' which branch off from the upper portion 22' and extend away from each other respectively towards the user's thighs. The under garment 10 may have the general shape of a brief-type under garment which surrounds a user's hips and genitals and extends down to separately surround upper portions of the user's thighs, but could be in the form of boxer shorts, briefs, a jock strap, etc. The garment may include an elastic waistband 26 that secures the under garment around a user's hips, one or more pockets 28 formed of any thin, light material which can receive the storage receptacles 6 therein and are secured to the user's thigh(s) or to portion(s) of the garment surrounding the user's thigh(s), and sleeves 30 made of cloth or thin, light material which respectively cover the lower portions 24' of the main body 2'. The sleeves 30 may be selectively securable around the lower portions 24' of the main body using an appropriate means such as zippers, buttons, or hook-and-loop fasteners, for example. The pockets 28 may have opening(s) through which the collection receptacles may be inserted and removed, and which may also permit the ends of the lower portions 24' of the main body 2' to extend therethrough into the receptacles. In other embodiments, the garment 10 may be an ordinary under garment with elongated pocket(s) 28 provided along the leg part(s) of the underwear, the pocket(s) may be attachable and detachable to the garment 10 by any suitable means, e.g., zipper(s), zip-lock(s), button(s), hook-and-loop fastener(s), etc. The garment 10 may be an ordinary pair of pants provided with side pocket(s) 28, such as discussed below in relation to another embodiment of the invention shown in FIGS. 4-6.

In some embodiments, a strap wraps around the user's waist similar to the elastic waistband 26, thereby holding an upper portion of the urinary collection apparatus 1 against the user. In other embodiments, a single strap may be affixed to the user's clothing to hold the apparatus 1 against the user. The strap may be affixed to the receptacle using fasteners, e.g., snaps or buttons. A single strap may be used, or two ore more straps may be used. In some embodiments, the strap may have a fastener to fix the strap to the user's clothing. For example, the strap fastener may be a clip such as used to connect stockings to a garter belt that may be clipped onto underwear to hold the receptacle in place. In a prefered embodiment, the upper end of the main body 2 is secured to the waistline of the garment by one or more of bonding using a releasable fastener such as a button, a hook, or a hook-and-loop type (e.g., Velcro®) fastener.

The urinary collection apparatus may be worn by a person while he/she sleeps, but for such use the collection receptacle 6 may be disposed separately from the user, e.g., lying on the floor, or hung on a hanger of known design.

The fastener 8 at the top of the main body 2' of the urinary collection apparatus 1' may be connected to the waistband 26, e.g., if the fastener 8 is a hook-and-loop type fastener one part of the fastener may be connected to the waistband and the other part of the fastener may be connected to the top of the main body.

Another modification as shown in FIG. 1 is to include more than one of the tubular ports 4 connected to upper portion 22 of the main body 2, which ports may have different sizes so that an appropriate size port may be used depending on the size of the user's penis, e.g., two different size ports 4 may be disposed opposite to each other on the main body, and the user would wear or secure the apparatus to his body such that the more appropriate sized port is disposed facing the user's penis.

Some possible modifications to the lower portion 24 of the main body 2 include: forming the storage receptacle integrally with the lower portion 24, such that they do not have to be operatively connected by the user; providing a reinforcement therewith, such as reinforcement rings 32 shown in FIG. 1B, which may be formed of thicker material provided in a spaced manner along the lower portion 24, e.g., every 2-6 cm; the lower portion may be adjustable in length, e.g., by having one or more extensions that can be connected to the lower end 12 via any appropriate fluid-tight means such as a zip-locking fastener; and the lower portion 24 may be closed-ended while the storage receptacle 6 is omitted such that any urine discharged into the main body 2 becomes stored in the lower portion 24 rather than in the storage receptacle, such as in the exemplary embodiment of the invention shown in FIGS. 4-6.

The Tubular Port

The urinary collection apparatus 1 includes at least one tubular port 4 projected from a wall of the upper portion 22 of the main body 2, and is configured to be disposed adjacent to the penis of a male user wearing the apparatus 1 so that the user may easily and conveniently insert at least a distal portion of his penis into the port when desiring to relieve himself into the apparatus. The tubular port 4 may be similar to a condom but it includes two open ends, i.e., one for insertion of the penis and the other which opens into the main body 2 for discharge. Further, the tubular port may include other features which make it suitable for use by persons having different size penises, as well as other features for preventing unintended leakage of urine. A first open end 38 of the port may project outwardly of the upper portion 22 while an intermediate portion of the port 4 is directly connected to the wall of the upper portion 22 and an opposite end 36 projects within the main body as shown in FIG. 1. Of course, many variations are possible, for example, the first open end 38 may be directly connected at and open into a wall the upper portion 22 as the entrance of the port and project inwardly into the main body 2 as shown in FIG. 1A. Inner diameter of the port may be about 4-5 cm with or without stretching, and its length 3-6 cm.

The tubular port 4 may be constructed of various types of material that is flexible, stretchable, thin, resilient, and the like, and thus is comfortable to wear. It may be constructed integrally with the main body 2 using the same material(s) that are used to form the main body. Alternatively, and given that the tubular port will normally experience more handling than the main body 2, the tubular port may be made separately from the main body, and of stronger material(s) than the main body, and subsequently connected to the main body by adhesive bonding, heat bonding, or in any other appropriate manner that will maintain a strong, fluid-tight connection between the components. For example, the tubular port 4 may be made from latex which is the most popular materials for condom so that it can stay secured on the penis like a latex condom. The tubular port 4 may also be made from non-latex material such as synthetic plastic materials, rubber, elastomers, etc. If the material(s) used for the tubular port 4 is/are stretchable, this helps to make the tubular port 4 adaptable to receive different size penises, and may help to prevent constriction, discomfort, and displacement of the penis relative to the port 4.

Alternatively and as shown in FIG. 1, the urinary receptacle 1 may have plurality of tubular ports 4, each of which has a different diameter and/or length to accommodate different sizes of penis. In such a modification involving multiple ports 4, the ports may be provided in spaced manner around a circumference of the upper portion, such that the user could secure the apparatus 1 to his undergarment with the appropriate one of the tubular ports 4 facing toward his penis so that use of the apparatus is facilitated.

As another alternative for making the tubular port usable by persons with different size penises, the end of the tubular port 4 into which a penis is to be inserted may be formed in an elongate, tapering shape which becomes smaller further away from where the port 4 connects to the upper portion 22 such as shown with broken lines in FIG. 1. The user may then, if necessary, cut off an appropriate terminal part of the projecting end such that the remaining part will have a suitable diameter for receiving the user's penis in a leak-proof manner. Similarly, the end of the tubular port 4 into which a penis is to be inserted may include a plurality of segments with different diameters such as small, medium and large extending continuously from each other such that the smallest segment is the terminal part of the end furthest from the upper portion 22, the medium section is next, and the largest section connects to the wall of the upper portion 22. The small section and medium section may be removed if needed by the user.

In any event, the tubular port 4 should have a sufficiently large inner diameter to accept a user's penis comfortably, e.g., it should loosely receive the user's penis and allow space for movement while the user is wearing the receptacle so that it is relatively comfortable, but should not have an overly wide diameter.

The penis insertion end of the tubular port 4 may have a circular entry mouth/lip which may be reinforced with resilient material, such as an elastic band 40, which draws the lip inwardly to some extent as shown in FIG. 1A, the cushion member wrapped around the retracted penis of those who are obese may make it easier for them use this invention The tubular port 4 effectively becomes elastic due to band 40, which seals against the penis and prevents the penis from unintentionally slipping out. The band 40 should not be so constrictive as to cause any undue pressure or discomfort on the penis.

To avoid the pressure on the contact point of the penis, a cushion member or material (not shown) may also be provided to the penis insertion end of the tubular port 4. The cushion member or material may be made of a soft material, e.g., fabric, foam rubber, gel, or other suitably soft material. In some embodiments, the cushion member may be made of a medical grade material, such as an anti-bacterial gel, latex, or silicone type material that may be washed so that the urinary receptacle is hygienic. The cushion member or material may be any suitable thickness, but preferably not so thick as to make the tubular port encumbering to a user or conspicuous when the apparatus 1 is worn by a user. The cushion member or material may be permanently or removably affixed to the penis insertion end of the tubular port 4. Alternatively, a water proof adhesive cushion member or material, such as a band-aid with built in cushion (e.g., 3M® Extra Cushion Flexible Foam Bandages), may be disposed around the penis before inserting to the tubular port 4 to avoid or minimize effect of constricting pressure caused by resilient material.

Because the tubular port 4 is made of the flexible and collapsible material, it gives the user no or minimal raise in the genital area when being used. The structure stated above makes it convenient to separate/remove a penis from the port without dislodging the port 4, even for physically active users. The penis may be pulled out from the main body 2 or tubular port 4 for natural voiding if desired by the user.

Collection Receptacle

Again the lower end 12 of the lower section 24 of the main body 2 may be open and operatively connected to a collection receptacle 6. The receptacle 6 may be bag or a bladder-like structure which is configured to be secured in a pocket 28 or otherwise secured to a user's thigh using an elastic or non-elastic strap that extends around the thigh, for example. The urinary collection apparatus 1 may include one or more collection receptacles 6. The collection receptacles 6 may be made of flexible and collapsible material like other components of the apparatus, would be of an appropriate size for holding several ounces of urine and may have some type of liquid absorbent therein such as the absorbents used in disposable diapers. For example, the collection receptacle 6 may have a flat, rectangular shape which has nominal thickness when empty and a size of 15×15×1.5 cm in dimension or larger when filled with urine. In some embodiments, for small incontinent leaking urine volume, the collection receptacle 6 may have a smaller size. Also, the separate receptacle 6 may be omitted and the lower portion 24 of the main body 2 may be closed-ended such that urine is stored directly in the lower portion of the main body.

For connecting the lower open end 12 of the lower portion 24 of the main body 2 to the collection receptacle 6, the receptacle 6 may have an opening 42 provided therein which is sized to receive the lower open end 12 therein in a fluid-tight manner, but which permits the receptacle to be easily separated from the lower open end 12 for being emptied or replaced as needed. For this purpose some type of seal 46 may be provided with the lower open end 12 and/or with the opening 42, which seal would require little or no manipulation by a user. Still further, the opening 42 of the receptacle 6 may include a seal which permits the opening 42 to be fluid-tightly closed when desired, e.g., when the receptacle 6 contains urine and is to be removed for replacement or emptying. For example, a zipper-lock type seal or a urine-resistant adhesive could be used.

The collection receptacle 6 and/or the lower portion 24 of the main body 2 may be equipped with a backflow preventer, not shown. The backflow preventer may be of any suitable design as long as it substantially prevents the flow of urine from the collection receptacle 6 back up toward the lower open end 12 of the lower portion 24 of the main body 2. Generally, backflow is minimized by disposing the collection receptacle 6 at a level significantly below the user's penis. Any suitable type of backflow preventer may be used, and furthermore, one or more of such backflow preventers may be present at any suitable position(s) in the system.

Female Adapter

Figure 3A:
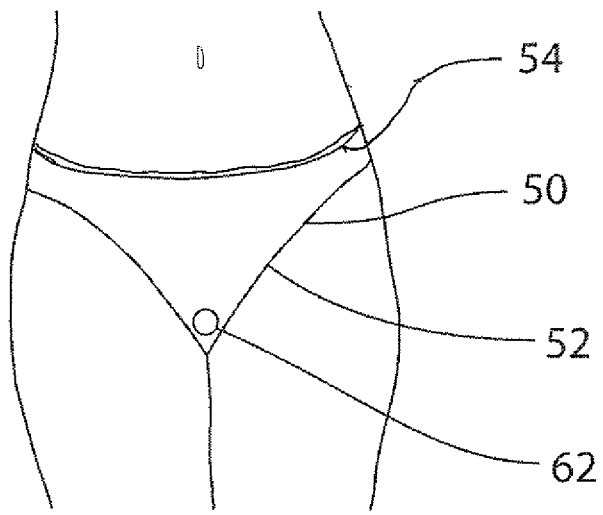
FIG. 3A is a perspective view of one portion of a female adapter which may be used with the urinary receptacle apparatus of FIG. 1.
Figure 3B:
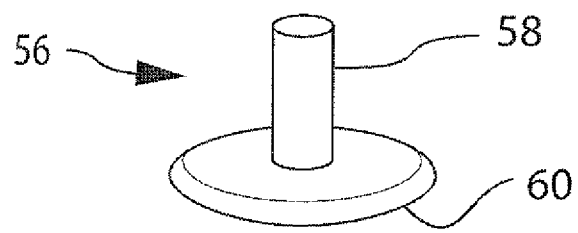
FIG. 3B is a perspective view of another portion of the female adapter which may be used with the urinary receptacle apparatus of FIG. 1.
Figure 3C:
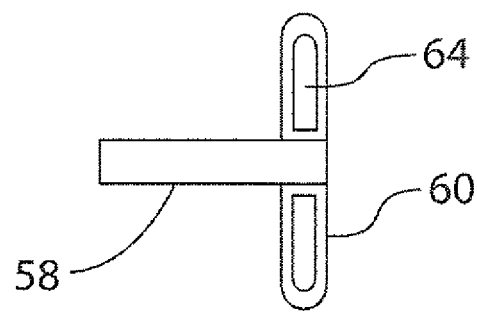
FIG. 3C is a cross section view of the other portion of the female adapter shown in FIG. 3B.

While the urinary collection apparatus 1 as discussed above is particularly suited for use by male persons, the present invention also includes an adapter an exemplary embodiment of which is shown in FIGS. 3A-3C, which adapter may be worn by female persons so that they also can use the urinary collection apparatus 1. The female adapter may include a first part 50 and a second part 56 which operatively connects to the first part 50 as shown. The first part 50 may be worn by a female similar to a panty, includes a main body 52 which is shaped to be provided in covering relation to the female genital area, an opening 62 formed through a central portion thereof, and an elastic waistband 54 connected to the main body and which the female user would wear about her hips or waist. The second part 56 has a base pad 60 and a spout 58 which projects from the base 60 and extends through the opening 62 when the second part 56 is joined with the main body 52 so that the spout 58 would project from the opening 62 such that the female user could easily manipulate the spout into the tubular port 4 of the urinary collection apparatus 1 similar to the male penis when the female user desires to discharge urine into the apparatus 1.

The base pad 60 may be disposed inwardly of the first part so that it contacts against the female user's urethral region and the spout 58 may be connected to a center of the base pad in a fluid-tight manner, such that it projects away therefrom. The base may be made of any material which would not cause discomfort to the female user when worn for several hours at a time, e.g., cotton, and may be provided with a soft pliable substance such as a gel for comfortable, secure and easy positioning over a female's urethral region. As depicted in FIG. 3C the base pad 60, may contain therein an air-filled bladder 64 or other elastic cushion material to minimize any discomfort to the user. The base pad 60 provides a sufficiently tight contact with the urethral region that any urine discharged by the user would be guided to flow through the spout 58. The base pad 60 may be flat and significantly wider than the spout 58 as depicted.

Embodiment without Separate Collection Receptacle

With reference to FIGS. 4-6, there is shown another exemplary embodiment of the urinary collection apparatus according to the present invention which does not include a separate collection receptacle, but instead the lower end of the lower portion 24 of the main body 2 may be closed or closable so that urine discharged into the main body through the tubular port 4 may be securely collected and retained in the lower portion 24. Additionally, means are provided whereby a user may simply and inconspicuously access the apparatus for any necessary or desired manipulation of same. Particularly, as depicted a side pocket 80 provided with a conventional outer garment for covering a user's lower body, such as pants, shorts, or a skirt, may be provided with an inner access opening 82 in an upper portion of the pocket and which opens to the inside of the outer garment, as well as a conventional outer access opening 81 of the pocket which opens to the outside of the garment such that a person wearing the garment may insert his/her hand into the pocket 80 through the opening 81. In this embodiment the closed-ended lower portion 24 of the main body 2 may be inserted into the pocket 80 through the inner access opening 82 where it may remain until user removes the urinary collection apparatus.

Further, a securing means may be provided with the pocket 80 and/or the lower portion 24 of the main body for securing the closed lower end of the lower portion 24 within the pocket. Such securing means may, for example, include an opening or slit 85 provided through an extension 87 of the lower closed end of the lower portion 24, which extension 87 is not in fluid communication with the rest of the lower portion 24, and a manipulatable coupler 84 secured within the pocket 80 and which may be easily manipulated by a user with one hand inserted into the pocket for operatively connecting the coupler 84 through and about the opening 85, and for opening the coupler to disconnect it from the opening 85 as shown in FIG. 6. Alternatively the opening or slit 85 may instead be provided in a member (not shown) connected to the inside of the pocket 80, while the manipulatable coupler 84 is connected to the lower end 24 of the main body. Further, other securing means could be provided for securing the closed lower end of the lower portion 24 within the pocket. Some other examples include a button (not shown) secured within the pocket 80 and which may be inserted through or withdrawn from the opening or slit 85 for selectively connecting and disconnecting the lower end of the lower portion 24 within the pocket, a hook-and-loop type fastener 84' as shown in FIG. 7 with respective portions connected to the closed lower end of the lower portion 24 and the pocket, etc. Also, the pocket 80 may have a second smaller pocket 83 attached to an inner surface thereof for storing small personal items or the like, and an additional securing means may be provided such that another part of the closed lower end of the lower portion 24 may be secured to the smaller pocket.

As shown in FIG. 5 the lower portion 24 of the main body 2 as retained inside of the pocket 80 may have an extended length which is accommodated by arranging the closed lower end in serpentine fashion within the pocket 80. An extended length is not necessary, however, and the lower portion 24 of the main body 2 may simply extend within the pocket 80 without any twists or turns, it may be constructed with a larger diameter to hold more liquid, etc. The closed-end lower portion 24 of the main body 2 may expand somewhat when filled with urine, but not so much that it would protrude and become conspicuous. Additionally, the pocket 80 may include some type of closure means 88 for being selectively connected to the lower portion 24 for closing off a section of the lower portion 24 which contains urine therein, as an added precaution for preventing the urine from moving back upwardly in the lower portion 24. Such closure means may also function as the securing means, or one part thereof, which secures the lower portion 24 in the pocket 80 and may, for example, comprise a manipulateable member similar to member 84, or any other appropriate closure means. For example, the closure means may comprise a spring lock mechanism (not shown), such as the spring lock mechanisms commonly used with apparel, e.g., as adjustable waistbands, adjustable hood bands, etc., having a cord which may be disposed around a part of the lower portion, a receiver having an opening defined therethrough and through which ends of the cord may be inserted, and a spring-biased member disposed within the receiver and which is normally urged into locking engagement with portions of the cord extended through the opening. For closing off the urine-containing part of the lower portion 24, the spring-biased member is compressed, e.g., between the user's thumb and index finger, the cord is extended around an appropriate part of the lower portion, the cord ends are inserted and pulled through the opening in the receiver so that an intermediate portion of the cord is drawn to a tight constriction about the part of the lower portion, and then the cord is locked in place by releasing compression on the spring-biased member so that it moves into locking engagement with the cord ends. Some portion of the closure means may also be connected to the pocket.

While in the embodiment of FIGS. 4-7 the apparatus does not include a separate receptacle and the lower end 12 of the lower portion 24 of the main body is closed such that urine is collected and retained in the lower portion, it is apparent and within the scope of the present invention that the embodiment of the invention as shown in FIG. 1 including the separate receptacle 6 could also be used together with the outer garment having the side pockets 80 as shown in FIGS. 4-5. For example, the receptacle 6 and the lower portion 24 of the main body 2 could be disposed and secured in the side pocket 80 during use of the apparatus 1.

As mentioned above the lower portion 24 of the main body may be closable rather than permanently closed. For example, the lower open end 12 of the lower portion may be provided with a zipper locking-type, fluid-tight sealing means (not shown) which a user may easily close or open as desired, e.g., the sealing means would be closed when the user desires urine to be collected and retained in the lower portion 24, and may be opened when the user desires to empty the collected urine from the lower portion. Thus, for example, urine may be collected and retained in the lower portion 24 (as situated within the pocket) when the user is unable to access a restroom or the like, but if the user later is able to access a restroom, he/she may conveniently remove the lower portion 24 from the pocket 80 by disconnecting the securing means which retains the lower portion in the pocket, and extending the lower portion 24 through the outer opening 81 of the pocket, after which the lower end 12 of the lower portion 24 may be disposed over a toilet and the sealing means opened to allow the collected urine to be discharged into the toilet. The sealing means again be closed and the lower portion re-secured within the pocket 80 for further use.

As can be seen from the various embodiments disclosed herein, the present invention provides a urinary collection apparatus 1 which is disposable, collapsible, flexible and easy to wear and use for collecting urine when individuals are unable to access a toilet, and is particularly suitable for people who have incontinence. The apparatus 1 is essentially inconspicuous when worn by an individual as it does not project to any significant extent away from the user's body. It is appropriate for use by physically active users. The urinary collection apparatus 1 makes it easy to separate/remove a penis from the receptacle without dislodging other parts of the apparatus. A male user's penis may be pulled out from the urinary receptacle for natural voiding, and similarly a female adapter can be used together with the apparatus 1 so that females may also use the apparatus. Further, the apparatus may be simply and inconspicuously manipulated by a user who is wearing the apparatus via access through a side pocket of an outer garment covering the user's lower body, such as pants. shorts, or a skirt.

While the present exemplary modes have been described in detail, those familiar with the art will recognize various alternative designs and embodiments within the scope of the following claims. While various embodiments may have been described as providing advantages or being preferred over other embodiments with respect to one or more desired characteristics, as one skilled in the art is aware, one or more characteristics may be compromised to achieve desired system attributes, which depend on the specific application and implementation. These attributes include, but are not limited to: cost, strength, durability, life cycle cost, marketability, appearance, packaging, size, serviceability, weight, manufacturability, ease of assembly, etc. The embodiments discussed herein that are described as less desirable than other embodiments or prior art implementations with respect to one or more characteristics are not outside the scope of the disclosure and may be desirable for particular applications.

The invention claimed is:

1. A urinary collection apparatus comprising:
    an elongate, tubular main body having an upper portion with a closed upper end and a lower portion with an open lower end;
    a tubular port projected from a wall of the upper portion and connected to the upper portion of the main body at a position spaced from the closed upper end, and configured to receive a user's penis therein in a fluid-tight manner such that urine discharged from a penis flows into the main body via the tubular port and is prevented from leaking from the upper portion of the main body above the tubular port;
    a urine collection receptacle connectable to the lower portion of the main body, and which receives and stores urine which flows out of the open lower end of the lower portion; and
    fastening means for securing at least one of the main body and the urine collection receptacle to a user or a garment worn by the user,
    wherein the main body, tubular port, and storage receptacle are formed of flexible, waterproof material and are configured to collapse flat against a user's body,
    wherein an end of the tubular port has an opening configured to receive the user's penis therein, and an elastic material is provided around a circumference of an open end of the tubular port which urges the circumference radially inward relative to other portions of the tubular port, and
    wherein the fastening means is provided at the closed upper end of the main body and is spaced away from the tubular port such that when the fastening means is attached to the garment worn by the user at the same level as a waistline of the garment, the tubular port is disposed at the same level as the user's penis, and
    wherein the tubular port is tapered along a length thereof with a largest diameter portion directly adjacent to the main body and a smallest diameter portion furthest away from the main body and having an end opening, whereby the end opening of the tubular port in configured to snugly fit the penis.

2. The urinary collection apparatus according to claim 1, wherein a plurality of the tubular ports are connected to the main body, and the plurality of tubular ports are disposed on the main body in spaced relation to each other and have different sizes.

3. The urinary collection apparatus according to claim 1, further comprising a pocket which selectively receives the storage receptacle therein, and fastening means for fastening the pocket to the user or to a garment worn by the user.

4. The urinary collection apparatus according to claim 1, wherein the urinary collection apparatus further comprises an undergarment configured to be worn by the user and to which at least one of the main body, the tubular port, and the storage receptacle may be selectively attached and detached.

5. The urinary collection apparatus according to claim 1, further comprising an undergarment configured to be worn by a female user, including a main portion which is configured to extend over the female user's urethral region, and a spout which is fluidly connected to main portion, projects away therefrom, and is configured to be selectively inserted in the tubular port.

6. The urinary collection apparatus according to claim 1, wherein the main body includes two of said lower portions having open lower ends and the urinary collection apparatus includes two of said urine collection receptacles, operatively connectable to the lower portions of the main body, respectively.

7. The urinary collection apparatus according to claim 1, further comprising an outer garment configured to be worn about a lower body portion of the user, the outer garment having pocket in which the collection receptacle may be disposed, the pocket includes a first access opening which opens outwardly of the garment and through which the user may insert a hand into the pocket, and a second access opening which opens inwardly of the garment and through which the lower portion of the main body may be inserted into the pocket, whereby the user may access the lower portion of the main body by inserting the user's hand into the pocket through the first access opening from outside the outer garment.

8. The urinary collection apparatus according to claim 1, further comprising:
    an undergarment configured to be worn by a female user, including a first portion which is configured to extend over the female user's urethral region and has an opening defined through an intermediate part thereof, and a second portion which is configured to be engaged with the first portion and includes a spout which extends through the opening and projects away therefrom,
    wherein the tubular port is configured to receive a projecting portion of the spout therein in a fluid-tight manner such that urine discharged from the spout flows into the main body via the tubular port.

9. A urinary collection apparatus comprising:

an elongate, tubular main body having an upper portion with a closed upper end, and a lower portion with a lower end that is permanently closed or selectively openable and closable;

a tubular port projected from a wall of the upper portion and connected to the upper portion of the main body at a position spaced from the closed upper end and connected to the main body and configured to receive a user's penis therein in a fluid-tight manner such that urine discharged from a penis flows into the main body via the tubular port and is collected in the lower portion of the main body;

an outer garment configured to be worn about a lower body portion of the user, the outer garment having pocket with a first access opening which opens outwardly of the outer garment and through which the user may insert a hand into the pocket, and a second access opening which opens inwardly of the outer garment and through which the lower portion of the main body may be inserted into the pocket, the pocket being of a size and shape to receive the inserted hand of the user; and fastening means for selectively securing the lower portion of the main body within the pocket, wherein:

the main body and the tubular port are formed of flexible, waterproof material and are configured to collapse flat against a user's body, the fastening means is configured to be manipulated by the user's hand as inserted into the pocket through the first access opening for securing and un-securing the lower portion of the main body which extends within the pocket through the second access opening while the outer garment is worn about the lower body portion of the user, whereby the user may access the lower portion of the main body by inserting the user's hand into the pocket through the first access opening from outside the garment, and the tubular port is tapered along a length thereof with a largest diameter portion directly adjacent to the main body and a smallest diameter portion furthest away from the main body and having an end opening, wherein the end opening of the tubular portion is configured to snugly fit the penis.

10. The urinary collection apparatus according to claim 9, wherein the fastening means includes a first member having a hole defined therethrough connected to one of the lower portion of the main body and the pocket, and a second member connected to the other of the lower portion of the main body and the pocket and which can be manipulated by the user's hand, as inserted into the pocket, between a secured position extended through the opening in the projecting member and an open position not secured through the opening in the projecting member.

11. The urinary collection apparatus according to claim 9, wherein the fastening means includes a projecting member with a hole defined therethrough connected to one of the lower portion of the main body and the pocket, and a button connected to the other of the lower portion of the main body and the pocket and which may be selectively inserted through the hole in the projecting member.

12. The urinary collection apparatus according to claim 9, wherein the lower end of the main body lower portion is selectively openable and closable, and the main body lower portion is configured to collect urine therein when the lower end thereof is closed.

13. The urinary collection apparatus according to claim 9, wherein the lower end of the main body lower portion is permanently closed, and the main body lower portion is configured to collect urine therein.

14. The urinary collection apparatus according to claim 1, wherein the elongate, tubular main body is tapered along a length thereof with a largest diameter portion in the closed upper end of the upper portion and a smallest diameter portion in the lower portion.

* * * * *